(12) United States Patent
Liao et al.

(10) Patent No.: US 10,076,582 B1
(45) Date of Patent: Sep. 18, 2018

(54) BABY FEEDING PRODUCT STERILIZATION DEVICE AND METHODS

(71) Applicant: Rayvio Corporation, Hayward, CA (US)

(72) Inventors: Yitao Liao, Hayward, CA (US); Doug Collins, Hayward, CA (US)

(73) Assignee: RAYVIO CORPORATION, Hayward, CA (US)

( * ) Notice: Subject to any disclaimer, the term of this patent is extended or adjusted under 35 U.S.C. 154(b) by 0 days.

(21) Appl. No.: 15/336,679

(22) Filed: Oct. 27, 2016

(51) Int. Cl.
  *A61L 2/10* (2006.01)
  *A61L 2/08* (2006.01)

(52) U.S. Cl.
  CPC .............. *A61L 2/10* (2013.01); *A61L 2/088* (2013.01); *A61L 2202/11* (2013.01); *A61L 2202/14* (2013.01); *A61L 2202/16* (2013.01); *A61L 2202/23* (2013.01)

(58) Field of Classification Search
  None
  See application file for complete search history.

(56) References Cited

U.S. PATENT DOCUMENTS

| | | | | |
|---|---|---|---|---|
| 5,305,876 A | * | 4/1994 | Brigham | A61C 19/002 206/459.5 |
| 6,524,447 B1 | * | 2/2003 | Carmignani | A61L 2/088 204/157.15 |
| 2014/0060095 A1 | * | 3/2014 | Shur | A61L 2/10 62/129 |
| 2014/0264070 A1 | * | 9/2014 | Bettles | A61L 2/10 250/430 |
| 2015/0069270 A1 | * | 3/2015 | Shur | F25D 17/042 250/492.1 |

\* cited by examiner

*Primary Examiner* — Kishor Mayekar
(74) *Attorney, Agent, or Firm* — Richard T. Ogawa; Ogawa P.C.

(57) ABSTRACT

A portable baby bottle sterilization device includes a housing having disposed therein an inner lining defining a bottle sterilization cavity, wherein the bottle sterilization cavity includes an opening, and wherein the inner lining is configured to receive one or more baby bottles therein through the opening, a power source, a plurality of UV LEDs coupled to the power source and to the inner lining, wherein the plurality of UV LED configured to provide UV-C light within the bottle sterilization cavity, and a processor coupled to the power source and to the plurality of UV LEDs, wherein the processor is configured to control intensity and duration of the UV-C light within the bottle sterilization cavity, and a cover coupled to the housing, wherein the cover is repositionable relative to the housing, wherein the cover can be positioned to removably cover the opening of the bottle sterilization cavity.

20 Claims, 5 Drawing Sheets

BABY FEEDING PRODUCT STERILIZATION DEVICE AND METHODS

BACKGROUND OF THE INVENTION

The present invention relates to the field of baby products. More specifically, the present invention relates to baby feeding product sterilization devices and methods.

Previously, baby feeding products, such as baby bottles, breast pumps, and pacifiers have been sterilized by boiling in hot water or in steam. Although these methods appear to be effective, the inventors believe such techniques are time consuming as they require constant supervision and such techniques are inconvenient as they require a stable location, e.g. a stove top or counter top, to hold the boiling water, steam, etc.

Some recent proposals have been made to sanitize baby bottles using UV light produced from a UV lamp, e.g. medium pressure mercury gas lamp. The inventors believe that such techniques are dangerous as they introduce mercury into the home and introduce a mercury source next to something that the baby will put into its mouth. The inventors believe that UV lamps are also fragile, as they rely upon brittle glass or quartz to contain the mercury gas, accordingly, the inventors believe that usage of UV lamps for baby products is not advisable. Further, when considering the use of UV mercury lamps for portable sterilization of baby products, the inventors believe that the fragile mercury bulb can be subject to extreme forces, e.g. dropping onto the pavement, and shatter. The stored mercury will thus be transferred to a baby's bottle nipple, pacifier, or the like. Another drawback is that UV light from mercury bulbs may undesirably generate ozone gas. In particular, because UV light from mercury bulbs generate a broad spectrum of UV light, including around 185 nm, a bottle sterilizer that relies upon mercury bulbs may produces ozone gas. Such a gas is particularly harmful to infants, and of course harmful to the environment.

In light of the above, what is desired are methods and devices for sterilization of baby products such as bottles, nipples, pacifiers, and the like without the drawbacks discussed above.

SUMMARY

The present invention relates to the field of baby product sterilization. More specifically, the present invention relates to baby product sterilization using UV-LEDs.

Embodiments of the present invention include a stationary or portable baby product sanitation device that can sterilize baby products such as bottles, pacifiers, nipples, breast pumps and accessories, straws, water bottles, spoons, forks, knives, tweezers, nail clippers, bows, chopsticks, sippy cups, teethers, dentures, or the like. Embodiments include a stationary or portable device including a UV sterilization chamber. Baby bottles can be placed in the UV sterilization chamber and exposed to UV light. In some embodiments, the UV light may be within the UV-C band (e.g. between about 200 nm to about 280 nm; the UV light may be within the UV-B (e.g. about 280 nm to about 300 nm; the UV light may substantially avoid UV light about the 180-185 nm range (ozone production range).

In various embodiments, the UV exposure time is typically short, e.g. in about 30 seconds, in about 60 seconds, within 30 to 60 seconds, less than about 2 minutes to 5 minutes, etc. depending upon the intensity of UV light provided. In some cases, if the UV exposure time is sufficiently short, e.g. less than a minute, the sterilization may be considered just-in-time or on-demand In various embodiments, solid-state UV light sources, e.g. UV-LEDs, are used to provide the UV light. The inventors believe that there are advantages of using solid-state device, as compared to a mercury gas tube. Such advantages include that solid-state devices have much lower power or voltage boost requirements, so that the sanitation devices may run on a battery. This greatly increases the portability, flexibility and convenience of such sanitation devices. Other advantages include that longevity of solid-state UV light sources is believed to be much greater than mercury tubes. Additional advantages are that solid-state UV LED light sources do not include hazardous materials, e.g. mercury; and the like. Such device may even be powered by solar cells for off-grid, portable applications, by crank power, external supply (e.g. USB, cigarette lighter, transformer to line voltage, line voltage, etc.). Still further advantages include because UV-LEDs can be produced having specified peak emission frequencies, the UV light output per power input efficiency is high, and the UV light can avoid undesirable light frequencies, e.g. about 180 nm to about 185 nm.

In one aspect of the invention, a portable baby bottle sterilization device is disclosed. One device includes a housing having an inner lining defining a bottle sterilization cavity, wherein the bottle sterilization cavity includes an opening, and wherein the inner lining is configured to receive one or more baby bottles therein through the opening, a power source, a plurality of UV LEDs coupled to the power source and to the inner lining, wherein the plurality of UV LED configured to provide UV light within the bottle sterilization cavity, and a processor coupled to the power source and to the plurality of UV LEDs, wherein the processor is configured to control intensity and duration of the UV light within the bottle sterilization cavity. An apparatus may include a cover coupled to the housing, wherein the cover is repositionable relative to the housing, wherein the cover can be positioned to removably cover the opening of the bottle sterilization cavity.

In some embodiments of the present invention, the bottle sterilization cavity may be formed of a UV reflective material, such as aluminum, stainless steel, Teflon, or the like; the bottle sterilization cavity may have a roughened or patterned surface to help scatter UV light in various directions; UV LEDs may be mounted upon any of the surfaces of the bottle sterilization cavity, or upon a projection within the bottle sterilization cavity (e.g. a fiber optic projection, a disco-ball-type projection, a rotatable projection, or the like) that may be disposed inside of a bottle to sanitize (e.g. a drying rack-type projection).

BRIEF DESCRIPTION OF THE DRAWINGS

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings in which.

DETAILED DESCRIPTION

Figure 1A:
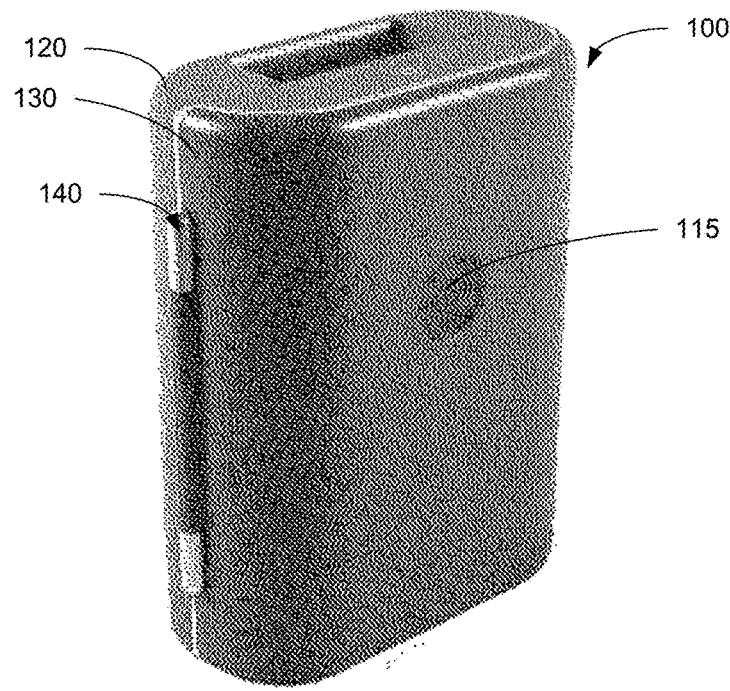
FIGS. 1A-1D illustrate a block diagram of various embodiments of the present invention.
Figure 1B:
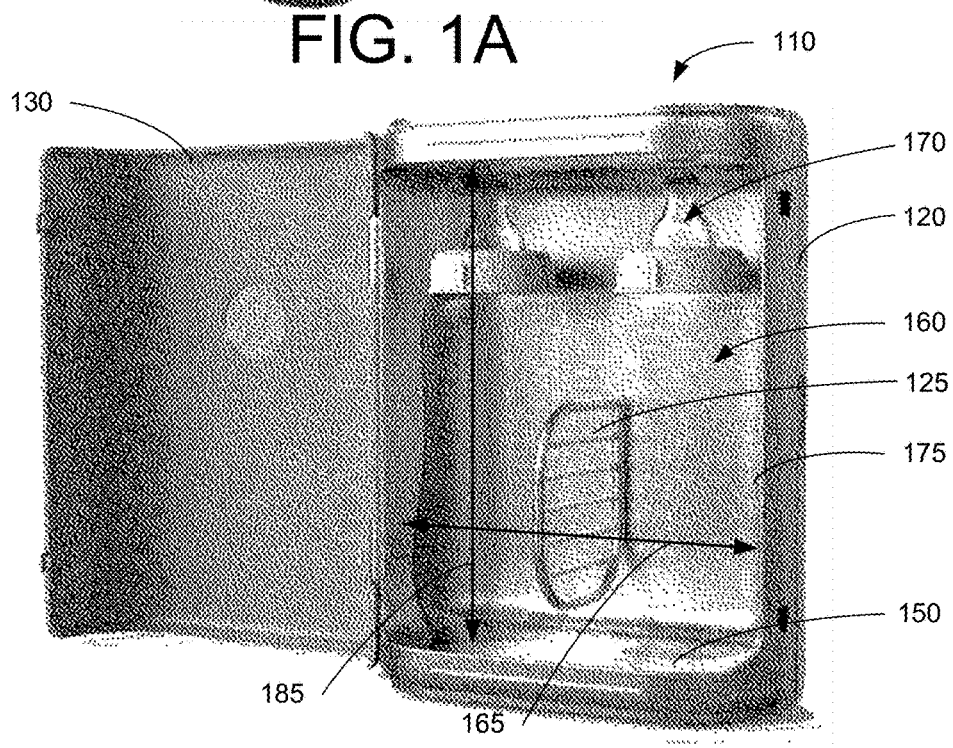

FIGS. 1A-D illustrates various embodiments of the present invention. More specifically, FIG. 1A illustrates an exterior view 100 of an embodiment, and FIG. 1B illustrates an interior view 110 of an embodiment of the present invention.

The embodiment illustrated in FIG. 1A includes a housing portion 120 and a cover portion 130. In this embodiments, housing portion 120 (e.g. back portion) and cover portion 130 are coupled via a hinge 140 enabling cover portion 130 to swing open and closed relative to housing portion 120. In other embodiments, cover portion 130 and housing portion 120 may have tracks enabling cover portion 130 to slide between a closed position (e.g. FIG. 1A) to an open position (e.g. FIG. 1B) relative to housing portion 120; cover portion 130 may be fully removable with respect to housing portion 120, for example cover portion 130 may be in the form of a screw-on/off lid, a friction fit lid, and a snap-lock lid; and the like. In various embodiments, housing portion 120 and cover portion 130 may be formed of plastic, metal, cloth on top of plastic or metal, rubber on top of plastic or metal (e.g. soft-touch coating), wood, fabric, or the like.

FIG. 1B illustrates interior view 110 when cover portion 130 is in an open position relative to housing portion 120. In this embodiment, housing portion 120 includes an inner lining 150 that forms a partial cavity 160 into which bottles 170 are placed. In this embodiment, an opening of partial cavity 160 runs along the length (long dimension) of bottles 170. In operation, bottles 170 are placed within partial cavity 160 bottle side-first.

In various embodiments, when cover portion 130 is in the closed position relative to housing portion 120, cover portion 140 covers partial cavity 160 and helps define a sterilization cavity. In other embodiments, different configurations for cover portion 130 and partial cavity 160 are contemplated, for example: cover portion 130 may be relatively flat, and partial cavity 160 may include higher sidewalls 175. In the example in FIG. 1B, the opening to partial cavity 160 runs along the length 185 of bottles 170. In another example, an opening to partial cavity 160 may run along the width 165 (cross-section) of bottles 170 upon a top portion 180 of housing portion 120. In such embodiments, bottles 170 are placed within partial cavity 160 bottle bottom first. In still other embodiments, different configurations for partial cavity 160 and cover portion 130 are contemplated, including combinations of the above (e.g. dutch-door).

In various embodiments, cover portion 140 and inner lining 150 may be fabricated from plastic, metal, plastic and metal, or the like. Further, cover portion 140 and inner lining 150 may include a material that reflects or that resists UV light, such as stainless steel, aluminum, Teflon (PTFE), or the like. In other embodiments, cover portion 140 and inner lining 150 may include a photocatalyst or UV-reactive material or coating such as TiO2. Such embodiments react of UV light exposure and generate one or more active species (e.g. oxygen species) that may react with any contaminants that reside upon the coating.

Figure 1C:
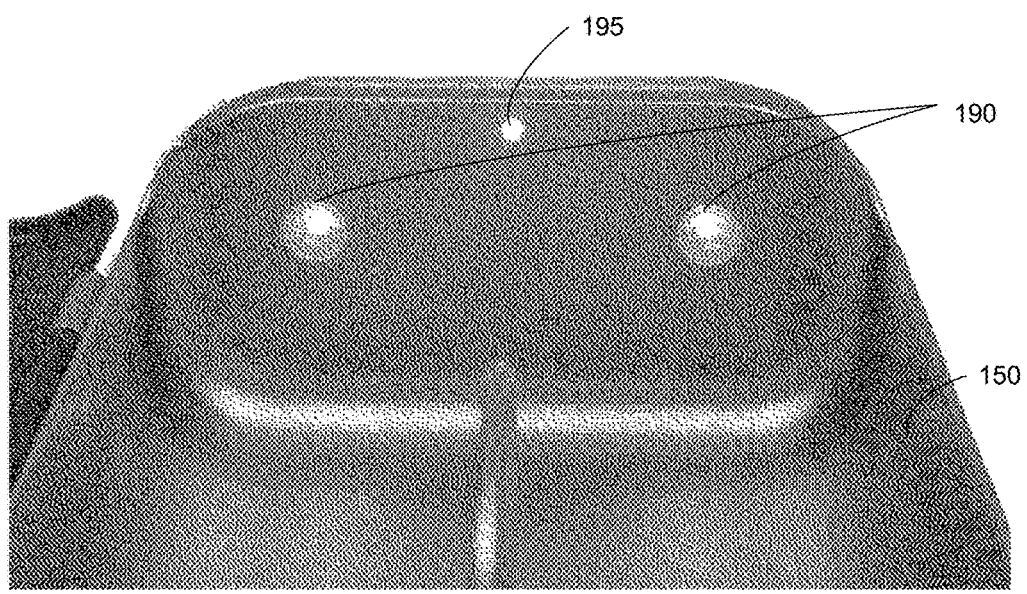
Figure 1D:
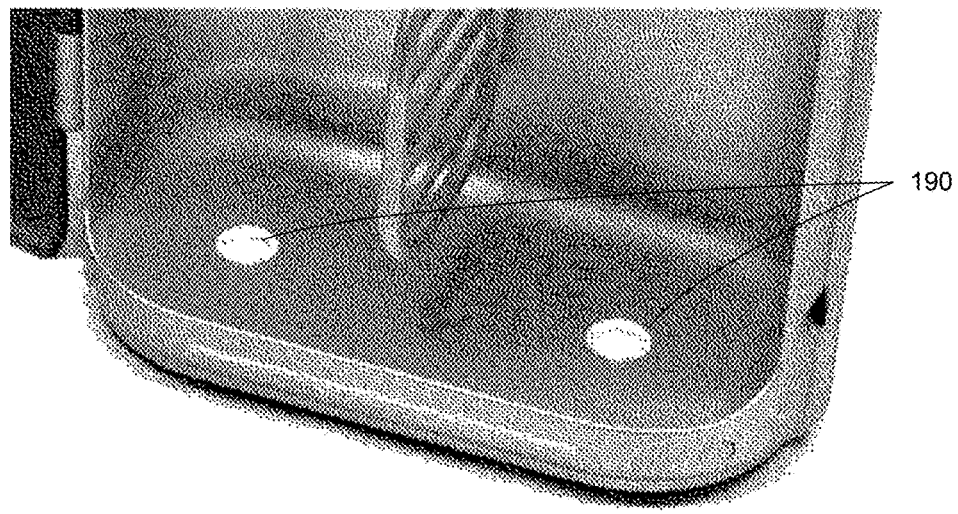

FIG. 1C-D illustrate close-up views of embodiments of the present invention. In the embodiment illustrated in FIGS. 1C-1D, inner lining 150 includes UV-LEDs 190 within an upper portion of inner lining 150 (FIG. 1C) and a lower portion of inner lining 150 (FIG. 1D). As will be described further below, UV-LEDs 190 are configured to provide UV light within the UV-C frequency band. UV-LEDs currently under development by the current assignee of the present invention, or others (as such devices become available in the future) may be used in various embodiments of the present invention. In the present configuration, as can be seen, a UV-LED is configured to provide UV-C light to a bottle 170 from the top and the bottom of each bottle, pacifier, etc. e.g. 170. In other embodiments, other configurations or arrangements of UV-LEDs may be added or used. For example, in some embodiments, UV-LEDs may be provided to provide UV light to the sides of bottles 170. The UV-LEDs may be disposed within inner lining 150, upon cover portion 130, upon sidewalls 175, or the like. In one specific embodiment, inner lining 150 and cover portion 130 may be provided with a grid of UV-LEDs, e.g. 3×3 grid, that provide UV light to the sides of each bottle 170 (e.g. FIG. 4). In still other embodiments, combinations of the above UV-LED configuration may be used, such as UV-LEDs that provide UV light to the top and bottom of bottle 170, as well as the sides of bottle 170.

In the embodiment illustrated in FIG. 1C, an internal light 195 (e.g. visible light LED) may be provided that provides visible light within partial cavity 160. In some embodiments, internal light 195 may provide a working light to the user. For example, when cover portion 130 is open with respect to housing portion 120, a white light may shine allowing the user to place or remove bottles 170 from partial cavity 160. This would be particularly useful in dark situations, e.g. a movie theater, a restaurant, a moving vehicle, or the like.

In other embodiments, internal light 195 may provide a visual indication of the progress or partial progress of a sterilization process. For example, when UV-C light is being provided within the sterilization cavity, internal light 195 may provide a blue-colored light, and/or when a sterilization process is completed, internal light 195 may provide a green-colored light. The color for internal light 195 can thus provide a user with an indication of the progress of a sanitation process. It is contemplated that a UV-blocking material may be placed in an opening 115 on cover portion 130 (in FIG. 1), through which the user can see the visible light from internal light 195. In some embodiments, opening 115 may be made of UV sensitive material and change color when the UV light is active. In such embodiments, a user would easily be able to tell when the UV light is on. In additional embodiments, a pattern, logo, or the like may be placed upon a plastic material over opening 115, and the pattern, logo, or the like may glow when the UV light is on.

In other embodiments, an indicator may be disposed directly upon the exterior of embodiments of the present invention to provide similar indications of the sanitation progress. For example, one or more LEDs may shine different colors to indicate different status: a blue light indicating that a UV sterilization cycle is in process; a red light indicating that a UV sterilization process has not been run (e.g. since the last time the cover portion 130 was closed), or that a UV sterilization process was not successfully completed (e.g. cover portion 130 was opened too soon); green light indicating that a UV sterilization cycle has successfully completed; and the like. In other embodiments, a status panel (e.g. LCD, OLED, or the like) may provide icons or textual messages that provide similar status indicators to the user. For example a wave-like icon or "UV" word may indicate a UV sterilization process; a stop-type icon or "DIRTY" word may indicate that the UV sterilization process did not complete; a thumbs-up icon or "OK" word may indicate the UV sterilization process completed successfully; or the like. In light of the present patent disclosure, one of ordinary skill in the art will recognize that many other combinations of lights, icons, or other indicators maybe be used to provide the functionality described above.

Figure 2:
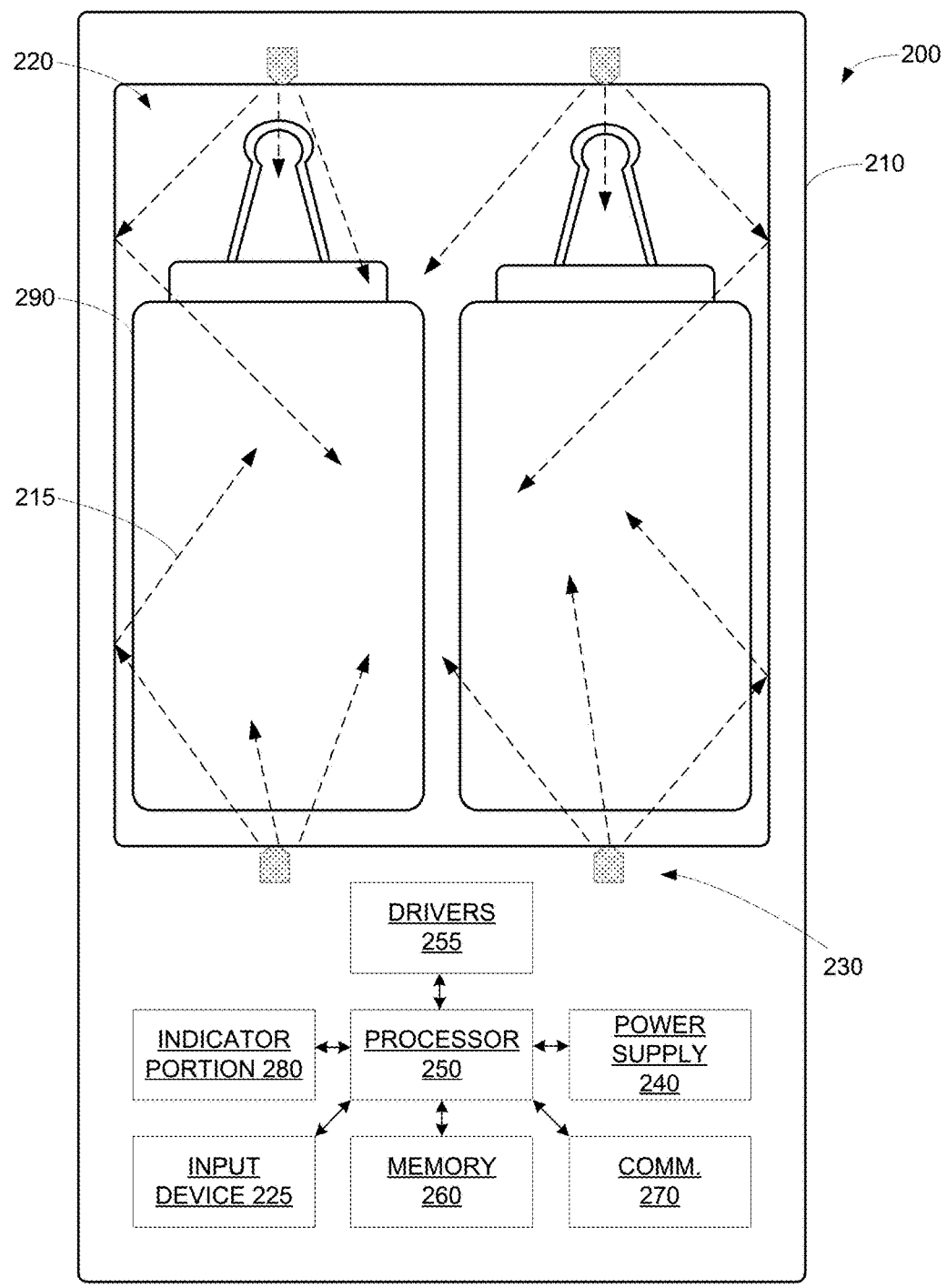
FIG. 2 illustrates a block diagram of various embodiments of the present invention.

FIG. 2 illustrates a block diagram of various embodiments of the present invention. In FIG. 2, a bottle sterilization device 200 is disclosed including a housing 210, a sterilization cavity (or chamber) 220, a plurality of UV LEDs 230, a power supply 240, a controller 250, a memory 260, a communications portion 270, a user indicator 280, and LED drivers 285. Inside sterilization chamber 220 are bottles 290 illustrated receiving UV-C light 215.

In various embodiments, sterilization device 200 is a hand-held, portable device that includes its own power supply 240, e.g. batteries. In some embodiments the batteries may be user-replaceable or rechargeable. Recharging may utilize any standard or non-standard port such as a mini-USB port, USB 3.0, or the like.

Within the bottle sterilization device, processor 250 controls the sterilization process, storage of data, and other operations of device. As shown, device 200 includes multiple solid-state UV-C light sources 230, e.g. LEDs, that provide UV-C light 215. In various embodiments, solid-state UV-C light sources 230, under development by the assignee of the present application, are used. Drivers 255 may be included in some embodiments for driving LEDs 230. Accordingly, the sterilization process is very quick, e.g. <2 minute, <30 seconds, within a range of about 30 seconds to about 60 seconds, or the like, and can be performed immediately before bottles 290 are required.

In various embodiments, sterilization cavity 220 may be constructed of one or more hard materials having an interior surface that reflects UV-C light. In some examples, as mentioned above, cavity 220 may include an aluminum material, stainless steel, a Teflon material, or the like. In other examples, cavity 220 may include a base surface made of plastic, glass, metal, or the like and have an interior coating of Teflon, silver, aluminum or other UV reflective material.

In FIG. 2, the shape of sterilization cavity 220 may be approximately the size of two bottles, and have a variety of shapes. In some embodiments, chamber 220 may be on the order of seven or eight inches tall, with a width of about six to eight inches wide, and with a depth of about two to three inches. In other embodiments, other dimensions of chamber 220 may be used, depending upon specific design or engineering requirements.

In some embodiments, an input device 225 may be provided to allow the user to manually begin a UV sterilization cycle. Input device 225 may thus be a push button, a switch, an icon on a display (e.g. an icon on a touchscreen), or the like. In some embodiments, input device 225 may be a switch associated with a cover portion (e.g. FIG. 1, 130). In such embodiments, when cover portion is closed, a UV sterilization cycle may be automatically performed immediately, or after an elapsed amount of time (e.g. five minutes)

In various embodiments, memory 260 may be used to store one or more sterilization routines that are executable on processor 250. As examples, memory 260 may store a UV sterilization process that varies an intensity of UV light for a specified amount of time: e.g. 100% UV output power for UV LED 230 for 2 minutes then 10% power for 20 minutes; 50% UV power for 5 minutes, 100% power for 2 minutes, and 50% power for 5 minutes; 25% power for 30 minutes; and the like. In various embodiments, the specific routine may be selected by the user (e.g. quick cycle, long cycle, intensive cleaning cycle, keep clean cycle, etc.). In other embodiments, device 200 may automatically determine the type of baby device being cleaned (e.g. bottle, rattle, pacifier, etc.) and/or the load (e.g. one bottle, two bottles, etc.), and dependent upon such determinations, processor 250 may automatically select the sterilization routine to use. In some embodiments, input device 225 may be used by the user to select the specific cycle, specify the load, or the like.

In various embodiments, memory 260 may be used to store usage data, indicating when a sterilization process is initiated, the sterilization cycle characteristics, and the like. These data together may be stored in a data log in memory 260.

In FIG. 2, a communications portion 270 is provided to support wired and/or wireless communication from sterilization device 200 to/from a remote device (e.g. via e-mail); a smart device (e.g. iPhone); or the like. In various embodiments, data transferred via communications portion 270 may include: usage data stored in memory 260, firmware data, sterilization routines, and the like. In various embodiments, wired connections may include: USB, Firewire, Apple Lightning, or the like. In addition or alternatively, embodiments may include wireless communication mechanisms, such as Bluetooth, Wi-Fi, NFC, ZigBee, Zwave, cellular data (e.g. 4G, LTE, 3G), IR, or the like. In one specific embodiment, sterilization device 200 may send a communication via Bluetooth to a smart phone to indicate that a sterilization routine has been successfully completed.

In some embodiments, an indicator portion 280 may include one or more indicator lights (e.g. LED), a display, as well as a speaker, a vibrating device, or the like. Indicator portion 280 may be used to provide feedback to the user for various conditions such as: when a sterilization process is being performed, when the sterilization process is finished, when sterilization device 200 is on or transmitting data, and the like. As discussed above, in some embodiments, a color, icon, or specific text may be used to provide visual feedback to the user. In other embodiments, a bell "ding" or microwave "beeps" sound may be played when a sterilization routine is successfully finished. In further embodiments, sterilization cavity 220 and/or a cover portion (e.g. FIG. 1, 130) may be constructed of a UV-sensitive material (e.g. plastic) that changes color upon exposure to UV light. In such embodiments, the UV sensitive material changes color when exposed to UV light, and the color is maintained for a certain amount of time after the UV light is withdrawn (e.g. one hour). In these embodiments, if the user opens sterilization cavity 220 and finds the plastic is red or pinkish, for example, the user will run a UV sterilization cycle; whereas if the user finds the plastic is greenish, for example, the user will know that a UV sanitization cycle was recently performed and the baby products have been sanitized.

Embodiments including additional functionality or less functionality are contemplated. In some embodiments a smart device (e.g. smart phone) may control operation of the sterilization device. For example, using an App on an iPhone, a user may direct the sterilization device 200 to begin a UV exposure cycle (e.g. directly (Bluetooth, ZigBee), text message, or the like), in response sterilization device 200 runs the sterilization routine, and then the sterilization device 200 indicates in response to the iPhone that the sterilization routine is finished and the baby product is ready to use. In some embodiments, the application on the smart device may track sanitation cycles as well as when device 200 is open/closed, etc. In these embodiments, the smart device may proactively remind the user when it is feeding time, remind the user that a sanitation cycle should be run, and the like. In still other embodiments, GPS functionality may be provided to give the user additional feedback as to where the sanitation process was performed.

Figure 3A:
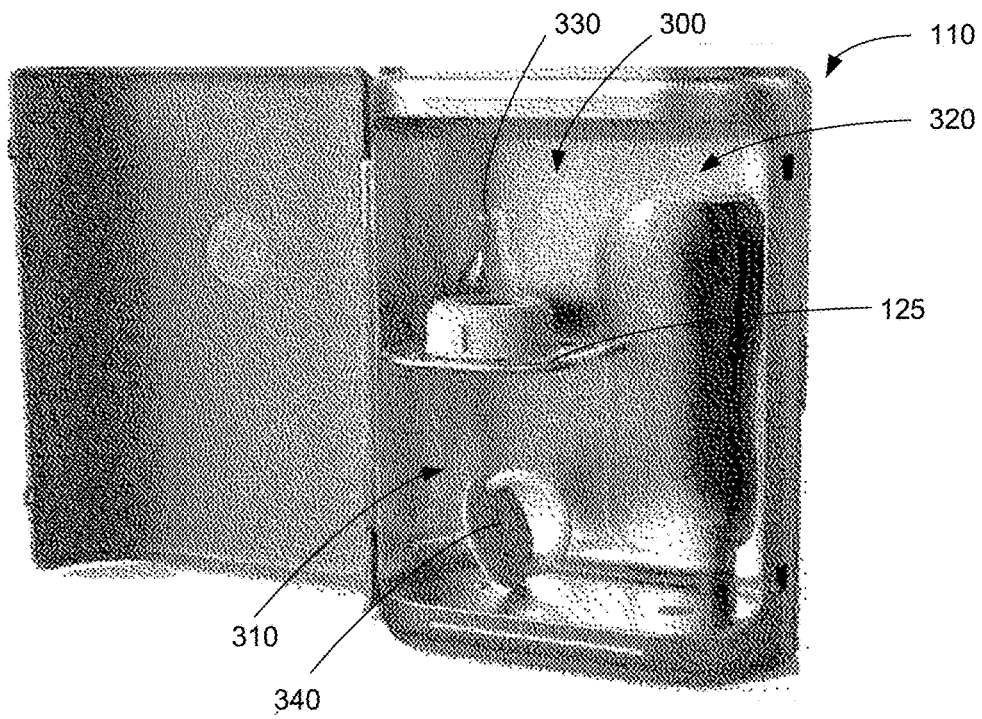
FIGS. 3A-3B illustrate additional embodiments of the present invention.
Figure 3B:
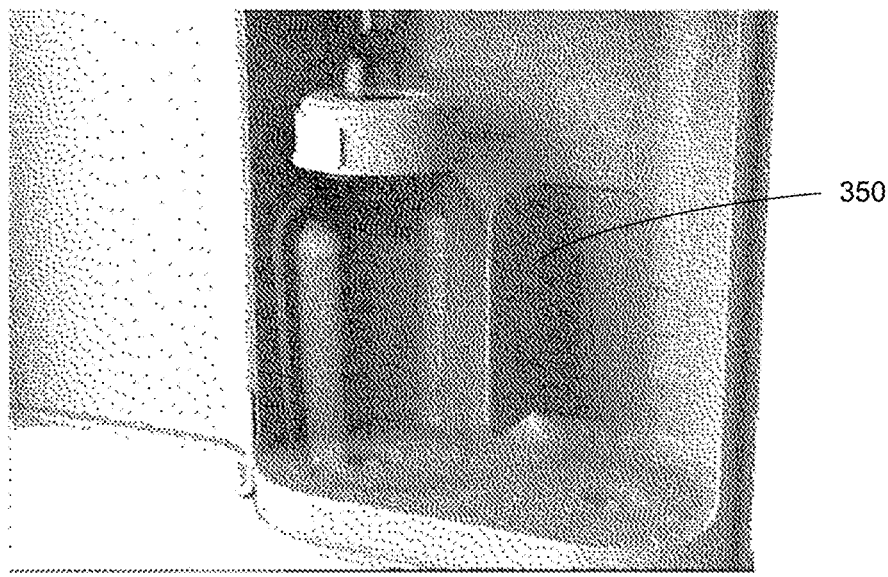

FIGS. 3A-3B illustrate additional various embodiments of the present invention. More specifically, FIGS. 3A-3B illustrates embodiments of a configurable divider or shelf to be used in embodiments of the present invention such as illustrated in FIG. 1. Illustrated in FIG. 1 is first configuration of a divider 125 separating bottles 170 within partial cavity 160. In various embodiments, divider 125 may be formed of a series of structures (e.g. metal wires, plastic, bamboo or the like). Alternatively, divider 125 may include a UV reflective material, (e.g. metal or metal plated), a UV reactive coating (e.g. TiO2), or the like. In the orientation illustrated in FIG. 1, divider 125 is illustrated partially separating bottles 170.

In the embodiment illustrated in FIG. 3A, as can be seen, divider 125 has be reoriented to divide partial cavity 160 into an upper region 300, a lower region 310, and a full-height region 320. As can be seen, upper region 300 is used to store a smaller item, e.g. bottle nipple 330, lower region is used to store a smaller item, e.g. a pacifier 340, and full-height region 320 is used to store a bottle. In such embodiments, divider 125 separates bottle nipple 330 from pacifier 340 so that surfaces of these baby products may be more fully exposed to UV-C light during a UV sanitation cycle.

In various embodiments, divider 125 may reoriented within partial cavity 160 by the user in a number of ways. In one specific example, the user may pull a square projection portion of divider 125 out of a square hole formed within the rear wall of inner lining 150; the user may rotate the divider 125 until it reaches a desired orientation, illustrated in FIGS. 1 and 3A, for example; and the user may push the square projection portion of divider 125 into the square hole to secure divider 125. In yet another embodiment, the projection portion of divider may be a cylinder or tapered cylinder, a hole within inner lining 150 may be a tapered cylinder or a cylinder, and divider is secured within the hold via friction fit. In such embodiments, the user simply pulls the divider out of the hole, and secures the divider back into the hole in any desired orientation. In other embodiments, a divider may include multiple projections, e.g. two or more, inner wall may include multiple holes, and the user can fit the divider into various holes to divide partial cavity 160 into a variety of regions.

In the embodiment illustrated in FIG. 3B, a divider 350 is illustrated that folds out from inner lining 360. In various embodiments, divider 350 may be a solid surface, a mesh-type surface, or a wire-type surface; and divider 350 may be made of the same material as inner lining 360 or other material (e.g. wire, metal). As can be seen in this embodiment, when not required, divider 350 may be folded against inner lining 360, and when required divider 350 may be flipped out. In other embodiments, additional dividers may be provided that help separate partial cavity 160 into upper regions and lower regions, as was illustrated in FIG. 3A, above. Such dividers may be used and folded-away in a similar way as described with divider 350. In light of the present disclosure, it is believed that one of ordinary skill in the art will recognize additional configurations are covered in various embodiments of the present invention.

Figure 4:
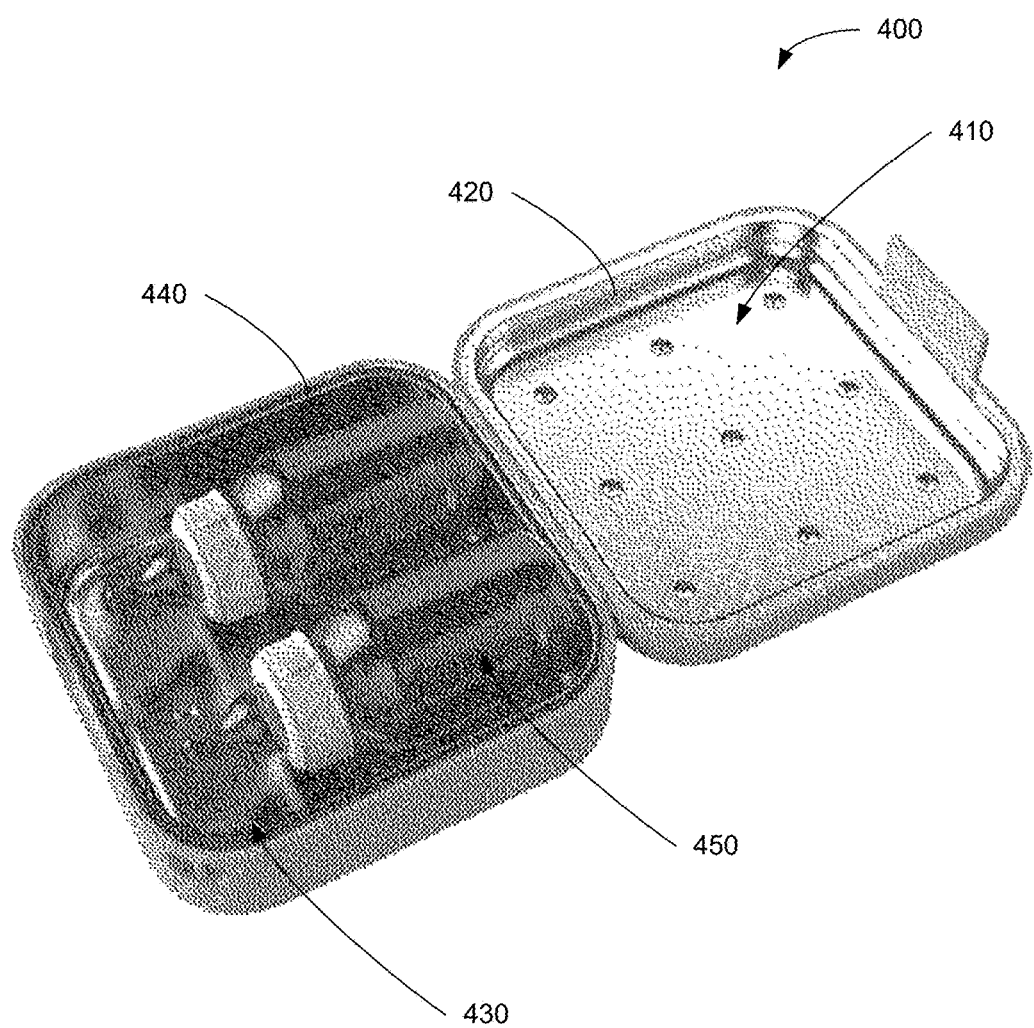
FIG. 4 illustrates an additional embodiments of the present invention.

FIG. 4 illustrates another embodiment of the present invention. In FIG. 4, an embodiment 400 is illustrated that includes a grid of UV LEDs 410 on a front cover 420 and UV LEDs 430 within a back wall of sterilization cavity 440. In other embodiments UV LEDs may also be incorporated into the top and/or bottom walls of sterilization cavity 440, as was shown in FIGS. 1C and 1D, or on sidewalls, etc. Further, in this example, half-sized bottles 450 are illustrated within sterilization cavity. It should be understood that other embodiments may be sized for full-sized bottles, as was illustrated in FIG. 1B, and adjustable dividers may also be used.

In various embodiments of the present invention, a sterilization process may include some or all of the following steps:

1. Receiving a baby bottle in a sterilization device;
2. determining a type of baby bottle or number of baby bottles automatically or manually and store in memory;
3. when the processor determines that the sterilization chamber is closed, secured, or otherwise enclosed, the user or the processor automatically initiates the sanitation process;
5. illuminating the UV-LEDs under direction of the processor, and the UV-C light shines upon the baby bottle; and
6 turning off the UV-LEDs off under direction of the processor when a desired amount of time has elapsed, the sanitation process following a sanitation profile has completed, and/or the sanitation process is stopped;
7. if completed, storing the completion data in the memory under direction of the processor;
8. subsequently, transmitting the time, indication of completion of the sanitation cycle, and the like from the memory via the communications path to a remote device.

In various embodiments, the sterilization chamber may be physically adapted for specific baby products such as a tall bottle, a sippy cup, a pacifier, a rattle, fork, spoon, knife, breast pump and peripherals, nipples, Straws, water bottles, tweezers, nail clippers, bows, chopsticks, teethers, dentures, glasses or the like.

In other embodiments, combinations or sub-combinations of the above disclosed invention can be advantageously made. For example, in other embodiments, the position of an opening and of a door may be situated on other portions of a sterilization chamber. For example, the sterilization chamber may be embodied as a drawer-type unit in a cabinet and UV LEDs may disposed on the top inside of the cabinet. In operation, after the drawer is pushed into the cabinet, the UV LEDs may be activated. In another embodiment, instead of a side-door hinge, as illustrated in FIGS. 1A-1B, a hinge may be upon the top or bottom of the housing and the cover may be a flip-up or a flip-down configuration. In some embodiments, one or more photodiodes may be included that can be exposed to the UV light from the UV LEDs. In operation, when UV light is present in the chamber, the photodiodes detect the UV light, and an indicator light may be activated on the exterior of the device, a sound may be played, or the like. Some of the embodiments described above may include a number of other capabilities, such as heating (e.g. IR LED, IR lamp, heating element, or the like), a fan or the like for venting and drying, followed by or preceded by a UV-light exposure cycle. In some embodiments, the device may also be used to sanitize other personal health or hygiene products, e.g. grooming tools, oral hygiene products, glasses, hearing aids, adult toys, or the like. Various embodiments may also be used to disinfect or maintain freshness of foods, especially for children, such as water stored in the bottles, fruits, vegetables, processed meats, or the like. Still further, embodiments may be in the form of a portable device, e.g. backpack, sleeve, suit case, etc., or in the form of a desk-top or counter-top device. The block diagrams of the architecture and flow charts are grouped for ease of understanding. However it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A portable baby bottle sterilization device comprises:
    a housing having disposed therein:
        an inner lining defining a bottle sterilization cavity, wherein the bottle sterilization cavity includes an opening, wherein the inner lining is configured to receive one or more baby bottles therein through the opening, and wherein the inner lining comprises a hole;
        a power source;
        a plurality of ultraviolet light emitting diodes (UV LEDs) coupled to the power source and to the inner lining, wherein the plurality of UV LED configured to provide UV-C light within the bottle sterilization cavity;
        a processor coupled to the power source and to the plurality of UV LEDs, wherein the processor is configured to control intensity and duration of the UV-C light within the bottle sterilization cavity;
    a movable divider disposed with the hole and configured to be oriented in the hole in a plurality of configurations, wherein in a first configuration, the movable divider partially separates the bottle sterilization cavity into a left and right configuration, and wherein in a second configuration, the movable divider partially separates the bottle sterilization cavity into a top and bottom configuration; and
    a cover coupled to the housing, wherein the cover is repositionable relative to the housing, wherein the cover can be positioned to removably cover the opening of the bottle sterilization cavity.

2. The portable baby bottle sterilization device of claim 1 wherein the inner lining comprises a relatively-UV-reflective material.

3. The portable baby bottle sterilization device of claim 2 wherein the relatively UV reflective material is selected from the group consisting of: aluminum, stainless steel, and metal-coated plastic.

4. The portable baby bottle sterilization device of claim 1 wherein the inner lining comprises a UV reactive material.

5. The portable baby bottle sterilization device of claim 1
    wherein the hole is characterized by a round cross-section; and
    wherein the movable divider is rotatable within the hole.

6. The portable baby bottle sterilization device of claim 1
    wherein the one or more baby bottles are characterized by a width and a height, wherein the height exceeds the width; and
    wherein the opening of the bottle sterilization cavity runs in a direct of the height.

7. The portable baby bottle sterilization device of claim 6
    wherein the one or more baby bottles are characterized by a top and a bottom; and
    wherein the plurality of UV LEDs are configured to provide the UV-C light directed to the top and the bottom of the one or more baby bottles.

8. The portable baby bottle sterilization device of claim 6 wherein the one or more baby bottles are characterized by a rear side; and
    wherein the plurality of UV LEDs are configured to provide the UV-C light directed to the rear side of the one or more baby bottles.

9. The portable baby bottle sterilization device of claim 8
    wherein the one or more baby bottles are characterized by a front side;
    wherein the cover comprises an additional plurality of UV LEDs configured to provide UV-C light; and
    wherein the additional plurality of UV LEDs are configured to provide the UV-C light directed to the front side of the one or more baby bottles.

10. The portable baby bottle sterilization device of claim 1
    wherein the housing comprises a visible-light LED; and
    wherein the visible-light LED is configured to provide a visual indicator when the UV-C light is provided within the bottle sterilization cavity.

11. The portable baby bottle sterilization device of claim 1
    wherein the housing comprises a visible-light LED; and
    wherein the visible-light LED is configured to provide a visual indicator after UV-C light has been provided to the bottle sterilization cavity for a pre-determined amount of time.

12. The portable baby bottle sterilization device of claim 1
    wherein the hole is characterized by a square shape cross-section;
    wherein a portion of the movable divider comprises a protrusion having a square shape cross-section; and
    wherein the protrusion is configured to be disposed within the hole.

13. The portable baby bottle sterilization device of claim 1 wherein the movable divider is selected from the group consisting of: plastic, metal, UV-C reflective material, UV reactive material.

14. The portable baby bottle sterilization device of claim 1 wherein the movable divider is pivotable with respect to the hole to change from the left and right configuration to enter the top and bottom configuration.

15. The portable baby bottle sterilization device of claim 1 wherein the housing comprises a shell having a material selected from the group consisting of: metal, plastic and cloth.

16. The portable baby bottle sterilization device of claim 1 wherein a height of the bottle sterilization cavity is within a range of about 7 inches to about 8 inches.

17. The portable baby bottle sterilization device of claim 1
    wherein the housing comprises a fan coupled to the power source; and
    wherein the fan is configured to induce airflow within the bottle sterilization device.

18. The portable baby bottle sterilization device of claim 1 further comprising a wireless communication portion coupled to the processor, wherein the wireless communication portion is configured to wireless indicate to a remote device that the UV-C light has been provided to the bottle sterilization cavity for a pre-determined amount of time.

19. The portable baby bottle sterilization device of claim 18
    wherein a wireless protocol associated with the wireless communication portion is selected from the group consisting of: Wi-Fi, near field communication (NFC), Bluetooth, ZigBee, Z-Wave, infrared (IR), cellular network, and 4G; and wherein the remote device is selected from the group consisting of: smart device, smart phone, and remote computer.

20. The portable baby bottle sterilization device of claim 1 wherein the housing further comprises a charging port configured to provide power to recharge the power source; and wherein the charging port is selected from the group consisting of: a universal serial bus (USB) port, a USB 3.x port, a micro USB port, a USB 2.x port, and a mini USB port.

\* \* \* \* \*